US00PP12568P2

(12) United States Plant Patent
Olesen et al.

(10) Patent No.: US PP12,568 P2
(45) Date of Patent: Apr. 23, 2002

(54) SHRUB ROSE PLANT NAMED 'POULDIRAM'

(76) Inventors: L. Pernille Olesen; Mogens N. Olesen, both of Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/273,167

(22) Filed: Mar. 19, 1999

(51) Int. Cl.[7] ..... A01H 5/00
(52) U.S. Cl. ..... Plt./103
(58) Field of Search ..... Plt./103, 102, 141, Plt./144

(56) References Cited

PUBLICATIONS

UPOV–ROM, 2001/01, Plant Variety Database, GTI Jouve Retrieval Software, citation for 'POULdiram'.*

Copy of Certificate of Grant of EU 6843 dated Nov. 6, 2000, and application EU 126/97 and proposal for variety denomination.*

UPOV–ROM, 2000/04, Plant Variety Database, GTI Jouve Retrieval Software, 2 citations for 'POULdiam', 1 citation for 'POULdiram'.*

* cited by examiner

*Primary Examiner*—Howard J. Locker

(57) ABSTRACT

A new garden rose plant which has abundant, semi-double white flowers that are self cleaning and are present throughout the season. The foliage is abundant, dark green, glossy and exceptionally disease resistant. This new and distinct variety has shown to be uniform and stable in the resulting generations from asexual propagation.

1 Drawing Sheet

SUMMARY OF THE INVENTION

The present invention constitutes a new and distinct variety of garden rose plant which originated from a controlled crossing conducted in the summer of 1990 between 'Bonica 82' and an unnamed seedling. The two parents were crossed and the resulting seeds were planted in a controlled environment. The new variety is named 'POULdiram'.

The new rose may be distinguished from its seed parent, 'Bonica 82', by the following combination of characteristics:

1. The seed parent has soft pink flowers which are 60 mm in diameter with 35 to 40 petals, while 'POULdiram' has white flowers which are 80 mm in diameter with 12–18 petals.

2. The seed parent is bushy and somewhat compact, while 'POULdiram' is taller with arching canes.

The new variety may be distinguished from its pollen parent, an unnamed seedling, created by the same inventors, by the following combination of characteristics:

1. The unnamed pollen parent has numerous, small, semi-double, light yellow flowers while 'POULdiram' has numerous, white flowers which are 80 mm in diameter.

2. The unnamed pollen parent has smaller foliage and a low growing spreading habit.

The objective of the hybridization of this rose variety for nursery and garden use was to create a new and distinct variety with unique qualities, such as:

1. Abundant, white flowers and recurrent blooming;

2. A shrub class rose with a vigorous, but uniform growth habit;

3. Glossy and disease resistant foliage which requires limited maintenance, making it ideal for use in landscapes;

4. Good growth, on its own roots, and as a traditionally budded plant.

This combination of qualities is not present in previously available commercial cultivars of this type and distinguish 'POULdiram' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULdiram' was selected by the inventors in the Spring of 1991 as a single plant from the progeny of the aforementioned hybridization.

Asexual reproduction of 'POULdiram' by traditional budding was first done by L. Pernille and Mogens N. Olesen in their nursery in Fredensborg, Denmark in August 1991. This initial and other subsequent propagations conducted in controlled environments have demonstrated that the characteristics of 'POULdiram' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULdiram'. Specifically illustrated in SHEET 1:

1. Stem showing branching and the attachment of leaves, buds, and flowers;

2. Flower bud, partially opened bud, and open bloom;

3. Flower petals, detached;

4. Sepals, and pedicel;

5. Flowering stem as well as a bare stem exhibiting thorns;

6. Leaves.

DETAILED DESCRIPTION OF THE VARIETY

The following is a description of 'POULdiram', as observed in its outdoor growth during September and October, 1998 in a field nursery in Jackson County, Oreg. Observations were conducted during October, 1998. Color references are made using The Royal Horticultural Society (London, England) Colour Chart, 1995, except where common terms of color are used.

For a comparison, several physical characteristics of the rose variety 'POULfan', a pink flowered rose variety from the same inventors described and illustrated in U.S. Plant Pat. No. 9,641 and issued on Sep. 10, 1996 are compared to 'POULdiram' in Chart 1.

CHART 1

| | 'POULdiram' | 'POULfan' |
|---|---|---|
| Petalage of flower bloom. | 12 to 18 petals under normal conditions. | Approximately 5 petals under normal conditions. |
| Flower petal color, upon opening, upper surface. | Red Group 36D. | Red Group 49A. |
| Flower petal color, open flower, upper surface. | White Group 155D. | Red Group 56C. |

Parents:

*Seed parent.*—'Bonica 82'.

*Pollen parent.*—Unnamed, unpatented seedling.

Classification:

*Botanical.*—*Rosa hybrida.*

*Commercial.*—Shrub.

FLOWER AND FLOWER BUD

Blooming habit: Recurrent.

Flower bud:

*Size.*—Upon opening, 30 mm in length from base of receptacle to end of bud.

*Bud form.*—Short, pointed ovoid.

*Bud color.*—As sepals unfold, Red Group 36A. At ¼ opening, Red Group 36D.

*Sepals.*—Yellow-Green Group 144B. Moderately strong foliaceous appendages on three of the five sepals. Inner surface of sepals are moderately pubescent while exterior surface is smooth. Stipitate glands are present only along the margins of the sepals.

*Receptacle.*—Surface: Shiny and smooth. Lacking stipitate glands. Shape: Urn-shaped. Size: Small. 4 mm (h)×4 mm (w). Color: Yellow-Green Group 144C.

*Pedicel.*—Surface: Moderate number of stipitate glands. Length: 25–40 mm average length. Color: Yellow-Green Group 144B. In cooler weather, intonations of Greyed-Purple Group 183D is present on pedicels and peduncles. Strength: Upright.

*Borne.*—Multiple buds per stem. Generally with 3–6 buds per flowering stem.

Flower bloom: Blooms maintain good color and form under wet and cold conditions.

*Fragrance.*—None.

*Duration.*—The blooms have a duration on the plant of approximately 3 to 5 days. Petals fall cleanly away from plant.

*Size.*—Average flower diameter is 80 mm when open.

*Form.*—Semi-double, flat to slightly reflexed.

*Shape of flower when viewed from the side.*—Upon opening, upper part: Flat. Upon opening, lower part: Flattened convex. Open flower, upper part: Flattened convex. Open flower, lower part: Concave.

*Petalage.*—12–18 petals under normal conditions with no petaloids.

Color:

*Upon opening, petals.*—Outermost petals: Upper Surface: Red Group 36D. Reverse Side: Red Group 36D. Innermost petals: Upper Surface: Orange-White Group 159C. Reverse Side: Orange-White Group 159D.

*Upon opening, basal petal spots.*—Outermost petals: Outer Side: Green-Yellow Group 1D. Inner Side: Green-Yellow Group 1C. Innermost petals: Outer Side: Yellow Group 2A. Variegation of Yellow Group 2B exhibited in center of petal base. Inner Side: Yellow Group 2B.

*After opening, petals.*—Petals: Upper Surface: White Group 155D. Reverse Side: White Group 155D.

*After opening, basal petal spots.*—Outermost petals: Outer Side: Yellow Group 3B. Inner Side: Yellow Group 3B. Innermost petals: Outer Side: Yellow Group 3B. The yellow color extends above the basal zones as a striation. Inner Side: Yellow Group 3B.

General tonality: On open flower, White Group 155D. There is no change in the general tonality during the life of the flower.

Petals:

*Petal reflex.*—Somewhat.

*Petal edge.*—Slightly ruffled.

*Shape.*—Deltoid shaped.

*Petaloids.*—Commonly none.

*Thickness.*—Thick.

*Arrangement.*—Informal.

Reproductive organs:

*Pollen.*—Color: Greyed-Orange Group 165B. Quantity: Average.

*Anthers.*—Size: Small. Color: Greyed-Yellow Group 161A. Quantity: Average.

*Filaments.*—Color: Yellow Group 4A, except at the base which is Orange-Red Group 33B.

*Stigmas.*—Stigmas slightly superior in location to anthers. Color: Greyed-Yellow Group 161C.

*Styles.*—Color: Red Group 47C below stigma, gradually lightening to Yellow-Green Group 145C below.

*Fruit.*—Large quantities of hips in the fall which are 15 mm (l)×15 mm (w). Color at maturity is Orange Group 28B.

PLANT

Plant growth: Tall shrub with slightly arching canes. Plant is tolerant of hot and dry conditions. When grown as a budded field grown plant on *Rosa multiflora* understock, the average height of the plant itself is 150 cm and the average width is 90 cm.

Stems:

*Color.*—Young wood: Yellow-Green Group 144B. Older wood: Yellow-Green Group 144A.

*Thorns.*—Incidence: Moderate numbers of thorns. Size: Average length: 9 mm. Color: Greyed-Orange Group 164A. Shape: Linear.

*Surface.*—Young wood: Smooth. Older wood: Smooth.

Plant foliage: Normal number of leaflets on leaves in middle of the stem: 5–7 leaflets.

*Leaf size.*—Medium. 100 mm (l)×65 mm (w).

*Quantity.*—Very abundant.

*Color.*—Upper Leaf Surface: Yellow-Green Group 147A. Lower Leaf Surface: Yellow-Green Group 147B. Juvenile foliage: Upper leaf surface: Yellow-Green Group 146A with moderate intonations of Greyed-Purple Group 183B on margins. Lower leaf surface: Yellow-Green Group 146B with moderate intonations of Greyed-Purple Group 183B on margins and undersurface. Anthocyanin: Location: Thorns, pedicels, stipules, and margins of leaflets. Color: Greyed-Purple Group 183B.

Plant leaves and leaflets:

*Stipules.*—Stipitate glands present along margins. The upper surface is covered with a fine pubescence. Size: 15 mm (l)×7 mm (w). Color: Yellow-Green Group 146B.

*Petiole.*—Length: 30 mm. Color: Yellow-Green Group 146B. Underneath: Occasional small prickles and some limited stipitate glands. Margins: Stipitate glands present in a moderate quantity.

*Rachis.*—Color: Yellow-Green Group 146B. Underneath: Prickles & stipitate glands present. Margins: Stipitate glands present.

*Leaflet.*—Edge: Serrated. Shape: Ovate. Texture: Glossy, thick, and leathery.

Disease resistance: Exceptional resistance to mildew, black spot, and Botrytis under normal growing conditions in Jackson County, Oreg.

Winter hardiness: POULdiram has been shown to be winter hardy in Fredensborg, Denmark and in Jackson County, Oreg.

We claim:

1. A new and distinct variety of rose plant of the shrub class, substantially as herein illustrated and described due to its abundant, white flowers, arching growth, exceptional disease resistance, and long period of bloom.

* * * * *

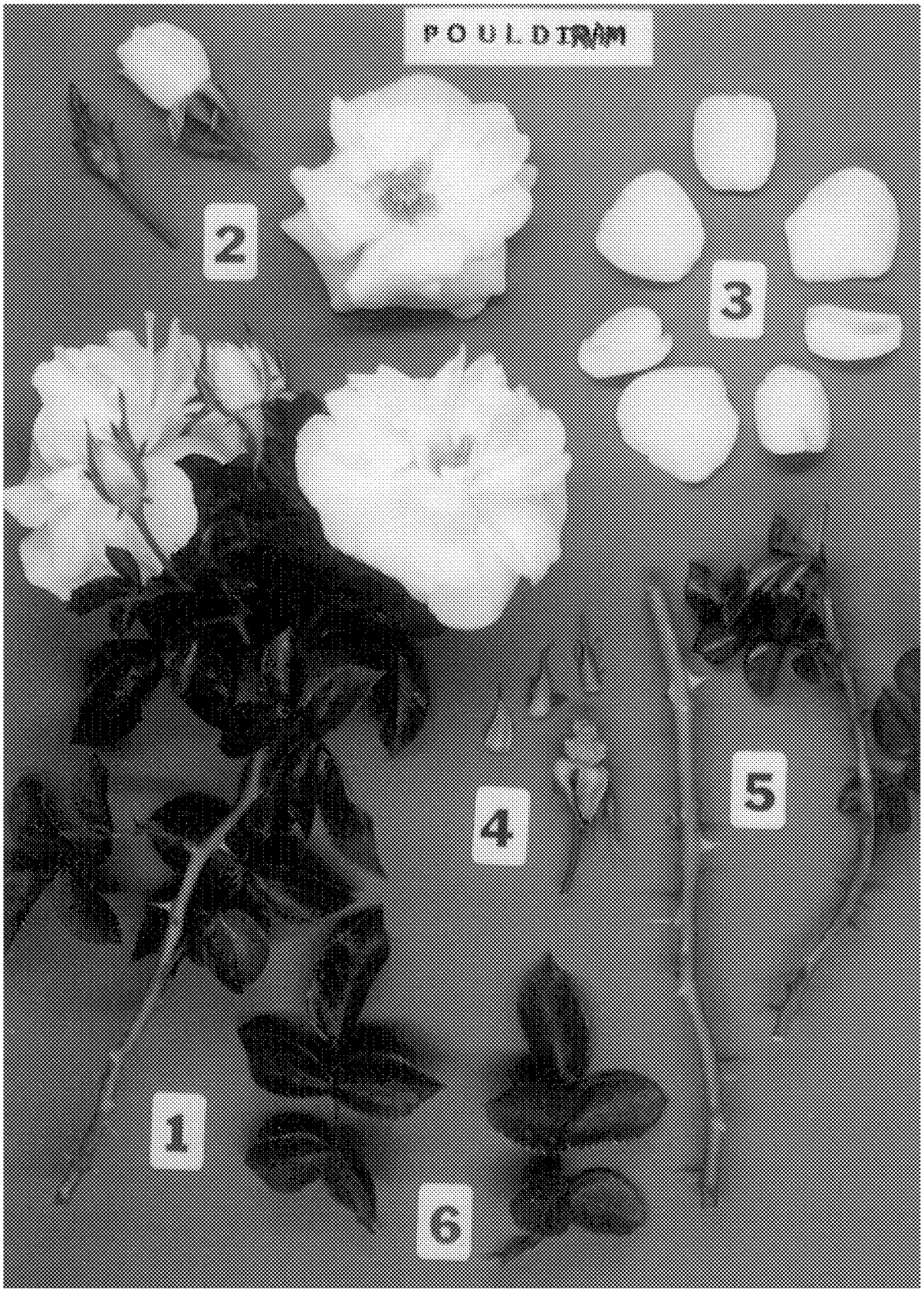
POULDIRAM
2
3
4
5
1
6